United States Patent [19]

Crutcher

[11] 4,156,684

[45] May 29, 1979

[54] GIBBERELLIN $A_4$ SEPARATION

[75] Inventor: Richard E. Crutcher, Waukegan, Ill.

[73] Assignee: Abbott Laboratories, North Chicago, Ill.

[21] Appl. No.: 885,936

[22] Filed: Mar. 13, 1978

[51] Int. Cl.$^2$ ............................................. C07D 307/77
[52] U.S. Cl. .................................. 260/343.3 G; 71/89
[58] Field of Search ................................. 260/343.3 G

[56] References Cited

U.S. PATENT DOCUMENTS 3,496,194  2/1970  Elson et al. .................... 260/343.3 G

OTHER PUBLICATIONS

Stainier et al., Chemical Abstracts 84:100674a, 1976.

*Primary Examiner*—Natalie Trousof
*Assistant Examiner*—Jane T. Fan
*Attorney, Agent, or Firm*—Paul D. Burgauer; Robert L. Niblack

[57] ABSTRACT

Gibberellin $A_4$ can be separated from the mixture of gibberellin $A_4/A_7$ by placing a dilute aqueous mixture thereof at the pH of at least 9 for one day or more and subsequent adjustment of the pH to below 5.5, thereby precipitating substantially pure $A_4$.

9 Claims, No Drawings

GIBBERELLIN $A_4$ SEPARATION

DETAILED DESCRIPTION OF THE INVENTION

Gibberellins are plant growth hormones with individual gibberellins being primarily useful for the promotion of certain plants or fruits or parts of certain plants. There are several dozen gibberellins known today, all structurally closely related to one another but some of them having more desirable properties than others.

The most prominently used gibberellins are identified as gibberellin $A_3$ and the mixture of $A_4/A_7$. Both of these are produced by cultures of *gibberella fujikuroi*, the fungus causing Bakanae disease in rice; the former, $A_3$ promotes stem growth in plants and fruits; the $A_4/A_7$ mixture promotes the growth and proper shaping of the fruit of certain plants.

It has not been determined unequivocally whether $A_4$ or $A_7$ is the more desirable component in the $A_4/A_7$ mixture since it always has been extremely difficult and expensive to separate the two. For instance, currently known techniques require the use of something like 1000 liters of various organic solvents to produce 100 g of substantially pure gibberellin $A_4$, a costly factor which is augmented by the need of chromatographic columns or plates required by the process of D. W. Pitel et al, Can. J. of Biochemistry, No. 49, pages 185–93 (1971).

It is, therefore, an object of the current invention to provide a practical separation for gibberellins $A_4$ from $A_7$; it is a further object of this invention to provide an inexpensive and efficient process for the separation of $A_4$ from $A_7$; it is a more specific object of this invention to provide a process for the isolation of substantially pure gibberellin $A_4$ from a mixture of gibberellins known to include $A_4$ and $A_7$.

These and other objects are accomplished by the process consisting essentially of placing a mixture of gibberellins $A_4$ and $A_7$ in an aqueous medium kept at a pH of 9–11 in a concentration of between 2.5 g and 25 g of said mixture per liter, at a temperature of between 10° and 100° C. for a period of at least 12 hours, subsequently lowering the pH to below 5.5, thereby precipitating substantially pure gibberellin $A_4$ from the liquid medium.

In the above definition, the requirement of keeping the pH at 9–11 is used to indicate that the pH either has to be adjusted from time to time during the reaction period or that a suitable buffer is used in connection with the base that is used to attain said pH range. The most practical base for this use is sodium hydroxide, although other alkali hydroxides could be used. Suitable buffers can be determined according to known principles for the required pH range; a practical choice is the use of disodium phosphate. Concerning the above concentration range, it should be kept in mind that about equal results can be obtained throughout said range; if the concentration is greater than or very close to 25 g of solids per liter, the subsequent precipitation of the $A_4$ component is likely to result in a gummy residue which will precipitate so fast that even vigorous stirring cannot prevent some inclusion of byproducts in the precipitate. When the concentration is below 2.5 g per liter, the final precipitation may not be completed and losses or gibberellin $A_4$ will occur. However, the precipitation step is preferably carried out under agitation to assure a more uniform distribution of the precipitating acid or acidic buffer.

The practical temperature for the above process is, of course, room temperature but within the range of 10°–30° C., a complete digestion of the $A_4/A_7$ mixture will take between 60 and 84 hours. If it is desired to accelerate the separation process, temperatures of between 30°–100° C. can be used without danger of adversely affecting $A_4$. At or near the boiling point of the aqueous medium, the reaction may be completed in 12–24 hours. After completion of the reaction, the pH is preferably lowered to below 5.5 by the addition of an inexpensive inorganic acid, e.g., hydrochloric acid. Other acids can be used but it is generally preferred to use the less costly inorganic acids. An excellent range for the precipitating pH is between 4 and 5.5 although no untowards effects are noticed if the pH is lowered to about 1 or 1.5. It is, however, necessary that the pH is at least as low as 5.5 to assure complete precipitation of the $A_4$ separated from the mixture while at the range of pH 1.0 and 4.0, essentially no additional material will come out of the solution.

It is obvious that the precipitate can be separated from the solids in various ways, most practically by filtration but under certain circumstances, it may be desirable to suction off the liquid, to centrifuge the mixture or simply to decant the supernatant followed by the addition of smaller portions of highly diluted acid at a pH of about 4.0.

In order to illustrate the process of the present invention, reference is made to the following example which, however, is not intended to limit the invention in any respect.

EXAMPLE 200 g of a mixture of gibberellin $A_4$ and $A_7$ (marketed under the name of PRO-GIBB ® by Abbott Laboratories) and 320 g of anhydrous dibasic potassium phosphate are dissolved in 8 liters of water. The pH is adjusted to 10 by the addition of the necessary amount of 40% sodium hydroxide and the resulting solution is allowed to stand at room temperature for three days. At that time, the pH of the solution is lowered by the addition of the necessary quantity of 8.5% o-phosphoric acid to attain a pH of 4.5±0.2 while stirring the mixture for one hour. Gibberellin $A_4$ precipitates during this period. The material is then filtered and the precipitate is washed with water, resulting in a purity of at least 95% of gibberellin $A_4$.

In most instances, the attained purity is satisfactory for the gibberellin $A_4$; it can directly be lyophalized or dried in an air dryer or oven and is ready for use. If a higher purity is required, the material can simply be recycled through the same process as described at which time the final purity is at least 99%.

The above process results in an irreversible degradation of gibberellin $A_7$, converting it to isogibberellin $A_7$ which is a soluble material at pH 1–5.5. This allows the separation of gibberellin $A_4$ which is insoluble at this pH. If desired, isogibberellin $A_7$ can be recovered essentially without loss from the filtrate or supernatant from which gibberellin $A_4$ has been separated.

Since the progress of the degradation of gibberellin $A_7$ depends on many factors such as its concentration, the temperature, the pH and probably also the nature of gibberellin mixture, it is often indicated to follow the progress of that degradation. This can be done by thin layer chromatography or high pressure liquid chromatography carried out with small samples of the reaction medium to show the absence of $A_7$. Thus, the terminal point of the degradation reaction can be expressed by the determinable absence of gibberellin $A_7$.

With the current invention it is now possible to obtain $A_4$ in a form free of $A_7$ impurities which, in turn, enables a determination of the true value of $A_4$ in its use as a plant growth hormone and the full development of its potential.

What is claimed is:

1. The process of separating substantially pure gibberellin $A_4$ consisting essentially in placing a mixture of gibberellin $A_4$ and $A_7$ in an aqueous medium maintained at a pH of 9–11 at a concentration of between 2.5 and 25 g of said mixture per liter at a temperature of 10°–100° C. until the absence of gibberellin $A_7$ can be determined, subsequently lowering the pH to below 5.5 and collecting the precipitated, substantially pure gibberellin $A_4$ from the liquid medium.

2. The process of claim 1 wherein the temperature is maintained between 10° and 30° C. and the reaction is allowed to continue for at least two days.

3. The process of claim 1 wherein said aqueous medium is adjusted to a pH of above 9 by the addition of sodium hydroxide and a suitable buffer.

4. The process of claim 3 wherein said buffer is disodium phosphate.

5. The process of claim 1 wherein the pH is lowered to below 5.5 by the addition of a suitable inorganic acid.

6. The process of claim 5 wherein said acid is hydrochloric acid.

7. The process of claim 5 wherein said acid is phosphoric acid.

8. The process of claim 5 wherein the reaction mixture is stirred while lowering the pH.

9. The process of claim 1 wherein said precipitated, substantially pure gibberellin $A_4$ is separated by filtration.